United States Patent [19]

Feiring

[11] Patent Number: 5,198,570

[45] Date of Patent: Mar. 30, 1993

[54] ARYLOXYFLUOROETHER ESTERS, PROCESSES FOR PREPARATION THEREOF, AND ALCOHOLS AND ACIDS FORMED THEREFROM

[75] Inventor: Andrew E. Feiring, Wilmington, Del.

[73] Assignee: E. I. du Pont de Nemours and Company, Wilmington, Del.

[21] Appl. No.: 474,586

[22] Filed: Jan. 31, 1990

[51] Int. Cl.$^5$ .............................................. C07C 69/76
[52] U.S. Cl. ........................................ 560/61; 560/59; 560/10; 560/15; 560/221; 560/56; 568/608; 568/609; 568/610
[58] Field of Search ...................... 568/610, 608, 609; 560/61, 59, 15, 221, 10

[56] References Cited

U.S. PATENT DOCUMENTS 3,739,016  6/1973  Quarles .................................. 560/62
4,281,092  7/1981  Breazeale ............................. 526/247

FOREIGN PATENT DOCUMENTS 203618  12/1986  European Pat. Off. .
293943  12/1988  European Pat. Off. .

OTHER PUBLICATIONS

D. C. Engalnd, J. Org. Chem., vol. 49, pp. 4007-4008 (1984).

Primary Examiner—Paul J. Killos

[57] ABSTRACT

Highly fluorinated aryloxyfluoroether esters, acids and alcohols, which are intermediates in the production of vinyl monomers, are provided. Also provided is a process for making aryloxyfluoroether esters by the base catalyzed addition of hydroxyaromatic compounds to perfluorovinylether esters.

35 Claims, No Drawings

ARYLOXYFLUOROETHER ESTERS, PROCESSES FOR PREPARATION THEREOF, AND ALCOHOLS AND ACIDS FORMED THEREFROM

FIELD OF THE INVENTION

This invention relates to aryloxyfluoroether esters, acids and alcohols, and to processes for preparation of aryloxyfluoroether esters. More particularly, this invention relates to aryloxyfluoroether esters, acids and alcohols useful as intermediates in the preparation of polymerizable monomers, and to the preparation of the esters by reaction of hydroxyaromatic compounds with perfluorovinylether esters.

BACKGROUND OF THE INVENTION

European Patent Applications 203,618 and 293,943 describe 1-benzoyl-3-aryl-urea derivatives having insecticide activity. Various substituted phenols are reacted with trifluorovinyl ethers under basic conditions (i.e., metal salts of the phenols). One group on the trifluorovinyl ether oxygen is (cyclo)alkyl or (cyclo)alkenyl, any of these optionally substituted with halogen. In a typical reaction, in 203,618, 2,6-dichloro-4-aminophenol reacts with perfluoro(ethyl vinyl ether) catalyzed by either sodium or sodium hydride in dioxane solvent, giving 3,5-dichloro-4-[2-(perfluoroethoxy)-1,1,2-trifluoroethoxy]aniline. However, the references do not disclose, groups in the trifluorovinyl ether other than (cyclo)alkyl or (cyclo)alkenyl in contrast to the ester group useful in the present invention.

Alcohols are also known to add to fluorinated vinyl ethers, see for example European Patent Application 254,632 and J. Org. Chem., vol. 49, pp. 7 4007-4008 (1984).

U.S. Pat. No. 4,281,092 reports the reaction of ammonia with a fluorinated vinyl ether ester. Instead of adding to the vinyl group, the ammonia adds to the ester group.

It is an object of the present invention to provide aryloxyfluoroether esters, acids and alcohols that are useful as intermediates in the preparation of monomers for polymerization. The present aryloxyfluorovinylether esters can be reduced by conventional means to form alcohols. These and other objects, features and advantages will become readily apparent upon having reference to the following description of the invention.

SUMMARY OF THE INVENTION

A compound of the formula $$Ar(ZCF_2CFHOR^1X)_p$$

wherein;

Ar is an organic radical containing one or more aromatic rings;

Z is oxygen;

each $R^1$ is independently perfluoroalkyl or ether, thioether, chloro, hydrogen, alkyl, or phenyl substituted perfluoroalkyl;

X is selected from the group consisting of $-CO_2R^2$ and $-CH_2OH$, wherein $R^2$ is hydrogen, alkyl or chloro, ether, thioether, tertiary amino phenyl, aralkyl, cycloalkyl, alkenyl or flouro substituted alkyl; and p is 1, 2, 3, 4 or 5; and provided that each Z is bonded to said aromatic rings.

Compounds of the invention may be prepared according to a process for the preparation of aryloxyfluoroether esters. The process comprises contacting a base, a perfluorovinylether ester of the formula $CF_2=CFOR^1CO_2R^2$ and a hydroxyaromatic compound of the formula $Ar(ZH)_p$, wherein:

each $R^1$ is independently perfluoroalkyl or ether, thioether, chloro, hydrogen, alkyl, or phenyl substituted perfluoroalkyl;

$R^2$ is alkyl or substituted alkyl;

Ar is an organic radical containing one or more aromatic rings which remains unchanged during the process;

Z is oxygen;

and p is 1, 2, 3, 4 or 5;

provided that each Z is bonded to said aromatic rings.

DETAILED DESCRIPTION OF THE INVENTION

The term "perfluoroalkyl" herein also includes perfluorocycloalkyl. The term "substituted perfluoroalkyl" herein includes substituted perfluorocycloalkyl and also includes any substituent that does not interfere with the reactions described herein that compounds containing these substituents undergo, and includes groups between aliphatic segments such as ether and thioether. Suitable substituent groups include, but are not limited to chloro, ether, hydrogen alkyl, substituted alkyl and phenyl. Ether groups are preferred substituents.

The term "alkyl" herein also includes cycloalkyl. The term "substituted alkyl" herein includes substituted cycloalkyl and also includes any substituent that does not interfere with the reactions described herein that compounds containing these substituents undergo, and include groups between aliphatic segments such as ether and thioether. Suitable substituent groups include but are not limited to, chloro, ether, thioether, tertiary amino and phenyl.

The organic radical Ar includes one or more aromatic rings. If more than one ring is present, the rings may be joined in a fused ring system as in naphthalene or anthracene, by a covalent bond as in biphenyl, and/or through a nonaromatic group as in a bisphenol, such as bisphenol-A. If more than one aromatic ring is present and more than one Z group is bonded to a particular Ar radical, the Z groups may all be bonded to one aromatic ring or distributed among 2 or more rings. Aromatic rings include carbocyclic and heterocyclic rings. The organic radical Ar may be substituted with any substituent that does not interfere with the reaction that formed the compound or a reaction that the compound will be subjected to. Suitable substituents include, but are not limited to, alkyl, alkenyl, alkynyl, halo, ether, tertiary amino, thioether and silyl. Suitable Ar organic radicals include, but are not limited to phenyl, phenylene, phenenyl, biphenyl, 4,4'-biphenylene, naphthyl, 1,4-naphthylene, 2,6-naphthylene, anthracenyl, pyridyl, 2-phenylethenylphenyl and the like. Preferred Ar groups are phenyl, phenylene, biphenyl, 4,4'-biphenylene, naphthyl and 2-phenylethenylphenyl.

In preferred compounds $R^1$ is $-[CF_2CF(CF_3)O]_n(CF_2)_m-$, wherein n is an integer from 0 through 5 and m is an integer from 1 through 10. In especially preferred compounds n is zero and m is 1 through 6 or m is 2 and n is 1 or 2. In the most preferred compound, n is 1 and m is 2.

Groups useful for $R^2$ include, but are not limited to, methyl, ethyl, propyl, butyl, benzyl, cyclohexyl, allyl, 2-ethoxyethyl, and 3,3,3-trifluoropropyl. Preferred $R^2$ groups are normal alkyl groups containing up to six carbon atoms.

Preferred values for p are 1 and 2, and 1 is especially preferred.

The compound $Ar(ZCF_2CFHOR^1X)_p$ is useful as an intermediate in the production of monomers for polymerization. Such methods are well known to those skilled in the art. When certain Ar groups are used and the $-CH_2OH$ is converted to its (meth)acrylic ester, and the (meth)acrylic ester is then polymerized, liquid crystalline polymers can result. See Experiment 1 for a typical procedure for producing a polymer.

A compound wherein X is $-CO_2R^2$ is an aryloxyfluoroether ester (or acid if $R^2$ is H), and where X is $-CH_2OH$ it is an aryloxyfluoroether alcohol.

Aryloxyfluoroether acids are produced by hydrolysis of the corresponding esters. Conditions for such hydrolyses are well known to those skilled in the art.

Aryloxyfluoroether esters are produced by a process, comprising, contacting a base, a perfluorovinylether ester of the formula $CF_2=CFOR^1CO_2R^2$ and an hydroxyaromatic compound of the formula $Ar(ZH)_p$ wherein $R^1$, $R^2$, Ar, Z and p are as defined above, provided that each Z is bonded to said aromatic rings, except $R^2$ is not hydrogen. All of the typical and preferred species for $R^1$, $R^2$ and p are as enumerated above, except $R^2$ is not hydrogen.

The reaction is conducted in the presence of a base. The amount of base used can be up to about an equimolar amount of the aromatic hydroxy groups ($-ZH$ groups) present in the reaction, preferably about 1 to 20 mole percent of the aromatic hydroxy groups present. Any base may be used as long as it can remove the proton from the aromatic hydroxy group. Typical useful bases are alkali metals and their hydrides, alkoxides, hydroxides and carbonates. Alkali metal hydrides and alkoxides are preferred bases.

The perfluorovinylether ester starting materials are prepared by methods well known to those skilled in the art, as described for example in U.S. Pat. Nos. 4,281,092 and 4,138,426, which are hereby incorporated by reference.

Any hydroxyaromatic compound may be used, that is a compound in which a hydroxy group is bound to a carbon atom of an aromatic ring. The hydroxyaromatic compound may be substituted with any substituent or group that does not interfere with the reaction. It is preferred that the hydroxyaromatic compound be chosen so that the aromatic hydroxy group(s) have a pKa of about 5 to about 12 as measured in water. Hydroxyaromatic compounds include, but are not limited to phenol, hydroquinone, resorcinol, bisphenol-A, 4-hydroxybiphenyl, 4,4'-biphenol, 1-hydroxynaphthalene, 2,6-dihydroxynaphthalene, 1,3,5-trihydroxybenzene, p-hydroxyaniline, 4'-methoxy-4-hydroxybiphenyl, 4-hydroxystilbene and 4-hydroxy-4'-methoxy-alpha-methylstilbene and 4'-hydroxy-4-methoxy-alpha-methylstilbene. Preferred hydroxyaromatic compounds include phenol, hydroquinone, 4-hydroxybiphenyl, 4,4'-biphenol, 4'-methoxy-4-hydroxybiphenyl, 4-hydroxystilbene and 4-hydroxy-4'-methoxy-alpha-methylstilbene.

Although the reaction can be carried out in the absence of solvent, it is preferred to use a solvent. Polar aprotic solvents are most useful, since they usually will dissolve all the reactants. Preferred solvents are dimethylformamide, tetrahydrofuran, dimethyacetamide, dimethylsulfoxide or mixtures thereof. Solvents, and indeed all starting materials, should be dry, since the presence of water may lead to undesirable side reactions. It is preferable to conduct the reaction under a dry inert atmosphere, such as under argon or nitrogen, to limit the introduction of moisture.

Reaction temperature is from about $-20°$ C. to about $50°$ C., preferably about $+20°$ C. to about $30°$ C. Pressure is not critical, and the process is usually conducted at atmospheric pressure. Reactants may be mixed in any order, but it is preferred to mix the base with the hydroxyaromatic compound and then with a perfluorovinylether ester. Mild agitation, although not critical, is useful for dissolving and mixing the ingredients.

The aryloxyfluoroether esters are isolated by methods well known to those skilled in the art. For example, the reaction mixture may be poured into acidified water, and the product extracted with an organic solvent such as ether. Purification may be accomplished by distillation, crystallization, chromatography and the like. Alternatively, if the aryloxyfluoroether ester is to be converted to an aryloxyfluoroether alcohol, purification of the ester may not be necessary as reduction of the crude ester to the alcohol may be satisfactory (infra).

Aryloxyfluoroether alcohols are prepared by reduction of the corresponding aryloxyfluoroether esters. Such reductions of esters to alcohols are well known to those skilled in the art. Reductions are often carried out by using sodium borohydride or lithium aluminum hydride as the reducing agents, see L. F. Feiser and M. Feiser, Reagents for Organic Synthesis, John Wiley & Sons, Inc., New York, 1967, pp 581–587 and 1049–1053. The isolation of the aryloxyfluoroether alcohols from these reactions is done by techniques well known to those skilled in the art.

In the Examples and Experiments the following abbreviations are used:

DMF—N,N-dimethylformamide
EVE—3-[2-(trifluoroethenyloxy)-1-trifluoromethyl-1,2,2,2-tetrafluoroethoxy]-2,2,3,3-tetrafluoropropanoic acid, methyl ester
NMR—nuclear magnetic resonance
THF—tetrahydrofuran In the following Examples and Experiments 4'-methoxy-4-hydroxybiphenyl was prepared according to Rodriguez-Parada and Percec (J. Polym. Sci., Polym. Chem. Ed. 24, 1363 (1986)), 4-methoxy-4'-hydroxy-α-methylstilbene according to Percec and Tomazos (J. Polym. Sci., Polym. Chem. Ed. 27, 999–1015 (1989); and 4-hydroxy-4'-methoxy-α-methylstilbene according to Percec and Tomazos (Macromolecules 22, 2062 (1989)). All other reagents are commercially available materials and were used as received.

EXAMPLE 1

Synthesis of the Addition Product of EVE with 4-Hydroxy-4'-methoxybiphenyl Using Sodium Hydride Catalyst

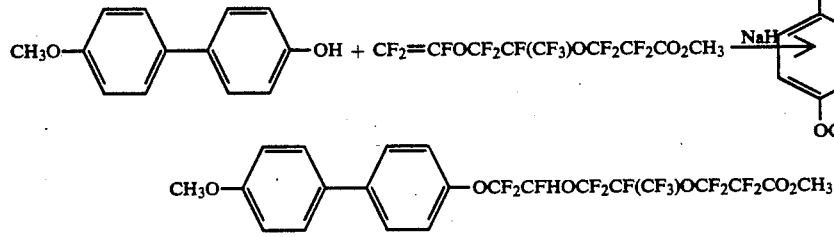

A solution of 5.0 g (0.025 mol) of 4-methoxy-4-hydroxybiphenyl and 0.075 g (0.003 mol) of sodium hydride (from 50% sodium hydride dispersion in mineral oil) in 80 mL of DMF was added over 1 hour to a solution of 27 g (0.027 mol) of EVE in 50 mL of THF and 20 mL of DMF at 20° C. The resulting mixture was stirred for 18 hours at room temperature under argon. The solution was poured into water and saturated with sodium chloride. The aqueous solution was extracted with ether. The ether solution was dried over anhydrous sodium sulfate and concentrated on a rotary evaporator. The residue was distilled in a Kugelrohr apparatus at 0.2 mm and 140°-150° C. giving 8.15 g (52%) of product as a waxy solid. Its proton NMR spectrum was obtained in CDCl$_3$ solution and is consistent with the desired product: δ 3.7 (s, 3H); 3.8 (s, 3H); 5.9 (doubled triplet, 1H); 6.6–7.5 (m, 8H).

EXAMPLE 2

Synthesis of the Bis-Addition Product of EVE with 4,4'-Biphenol Using Sodium Hydride Catalyst

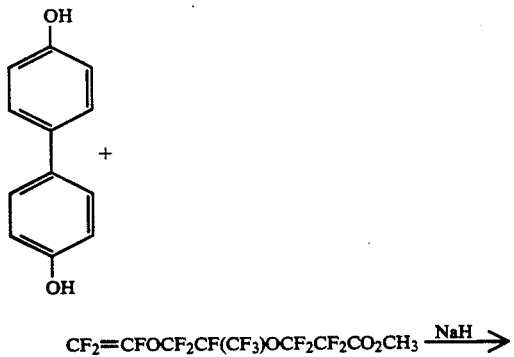

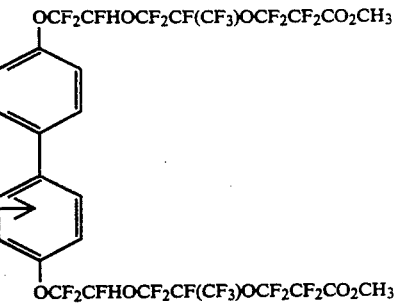

4,4'-Biphenol (9.31 g, 0.05 mol) was added to a suspension of 0.2 g (0.0083 mol) of sodium hydride in 90 mL of DMF. The clear solution was transferred to an addition funnel and added dropwise over 5.5 hr to a solution of 50 g (0.118 mol) of EVE in 100 mL of anhydrous THF at 23°-27° c. The resulting solution was stirred at room temperature for 5 days, then poured in 1 L of ice water. The aqueous mixture was saturated with sodium chloride and extracted with ether. The ether was dried over anhydrous sodium sulfate and concentrated on a rotary evaporator to 57.9 g of oil. The oil was chromatographed over silica gel and eluted with 1:6 ethyl acetate:hexane. The collected material was distilled in a Kugelrohr apparatus at 190° C. and 0.2 mm pressure to give 20.4 g of the bis-adduct. Proton NMR (δ,CD$_2$Cl$_2$) 3.95 (s, 6H); 6.15 (doubled triplet, 2H); 7.4 (q, 8H). Fluorine NMR (δ, CD$_2$Cl$_2$) −80.5 (6F, CF$_3$); −82.5 to −88.0 (12F, CF$_2$'s); −122.0 (4F, CF$_2$); −144.9 (2F; CFH); −145.6 (2F, CF). Anal. Calcd. for C$_{30}$H$_{26}$F$_{26}$O$_{10}$: C, 34.97; H, 1.57; F, 47.94. Found: C, 34.84; H, 1.52; F, 47.66.

EXAMPLE 3

Synthesis of the Addition Product of EVE with 4-Hydroxy-4'-methoxybiphenyl Using Potassium t-Butoxide Catalyst and Reduction to the Corresponding Alcohol

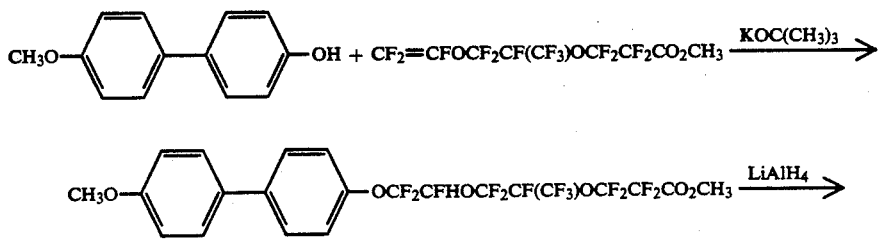

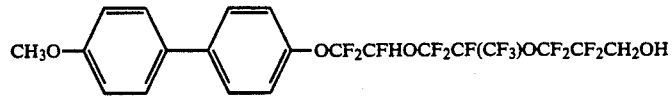

To a solution of 5.0 g (0.025 mol) of 4-methoxy-4'-hydroxybiphenyl in 15 mL of DMF was added 0.52 g (0.0046 mol) of potassium t-butoxide. After stirring for 10 minutes, this solution was added over 1 hr to a solu-

EXAMPLE 4

Synthesis of the Addition Product of EVE with 4-Hydroxy-4'-methoxy-α-methylstilbene

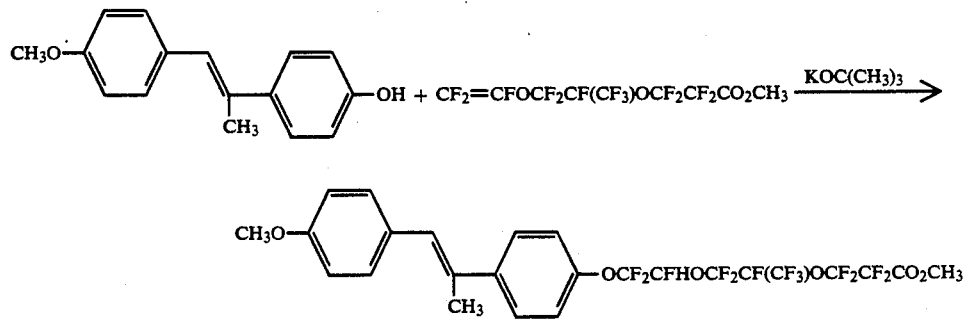

tion of 15.1 g (0.036 mol) of EVE in 10 mL of anhydrous THF while maintaining the solution temperature at 20°-22° C. After addition, the solution was stirred at room temperature for 5 hr and poured into 200 mL of ice water containing three drops of concentrated hydrochloric acid. The aqueous mixture was extracted with 3×200 mL of ether. The combined ether extracts were dried over anhydrous magnesium sulfate and concentrated on a rotary evaporator to 20.4 g of oil. Kugelrohr distillation of the oil at 0.2 mm gave, after removing a small forerun, 13.3 g (86%) of the ester product which distilled at a bath temperature of 160°-170° C. This product was dissolved in 50 mL of ether and added over 5 minutes to a suspension of 3.54 g of lithium aluminum hydride in 150 mL of ether which was cooled to 10°-20° C. in an ice bath. After the addition was complete, the mixture was stirred at room temperature for 4.5 hours. The reaction was quenched by the addition of 3.5 g water, 3.6 mL of 15% aqueous sodium hydroxide and 11 mL of water. The slurry was filtered and the solid washed with 2×100 mL of ether. The combined filtrate and washings were dried over anhydrous magnesium sulfate and concentrated on a rotary evaporator to 11.77 g of oil. Kugelrohr distillation of the oil at 0.2 mm and 150°-170° C. gave, after a small forerun, 11.19 g of the waxy alcohol. The overall yield from the two steps is 75.3%. Proton NMR (δ, CD$_2$Cl$_2$) 2.36 (t, 1H); 3.8 (s, 3H); 4.03 (tripled doublet, 2H); 6.11 (doubled triplet, 1H), 7.37 (q, 8H). Fluorine NMR (δ, CD$_2$Cl$_2$) −80.2 (3F); −83 to −87.3 (6F); −126.3 (2F); −144.8 (1F); −145.5 (1F). Anal: Calcd. for C$_{21}$H$_{15}$F$_{13}$O$_5$: C, 42.44; H, 2.54; F, 41.56. Found: C, 42.48; H, 2.58; F, 40.80.

Potassium t-butoxide (0.34 g, 0.0031 mol) was added to a solution of 4.99 g (0.021 mol) of 4-hydroxy-4'-methoxy-α-methylstilbene in 25 mL of DMF. The solution was stirred for 10 min and added over 55 min to a solution of 14.88 g (0.035 mol) of EVE in 30 mL of THF. Additional DMF (5 mL) and THF (15 mL) were used to rinse. The resulting solution was stirred for 2 hr at 26° C. and 0.5 hr at 45° C. The solution was diluted with ice water and decanted from a deposited gum. The gum was dissolved in methylene chloride and the aqueous solution was extracted with additional methylene chloride. The combined methylene chloride solutions were dried over anhydrous magnesium sulfate and evaporated to 15.9 g of oil. The oil was chromatographed over silica gel, eluting with 2-L of hexane, followed by 1-L of 0.3% ethyl acetate in hexane and 1-L of 0.5% ethyl acetate in hexane. Fractions 24 to 37 were combined and re-chromatographed on a 6.4 cm diameter by 35.6 cm long column of silica gel, eluting with 0.1 to 0.3% of ethyl acetate in hexane to give 5.06 g (39%) of product as a waxy solid. Proton NMR (δ, CD$_2$Cl$_2$) 2.27 (d, 3H); 3.83 (s, 3H); 3.95 (d, 3H); 6.17 (doubled triplet, 1H); 6.92 (d, 2H); 7.19 (d, 2H); 7.35 (d, 2H); 7.55 (d, 2H). Fluorine NMR (δ, CD$_2$Cl$_2$) −80.2 (3F); −82.5 to −87.4 (6F); −121.5 (2F); −144.8 (1F); −145.4 (1F).

EXAMPLE 5

Synthesis of the Addition Product of EVE with 4-Methoxy-4'-hydroxy-α-methylstilbene and Reduction to the Corresponding Alcohol

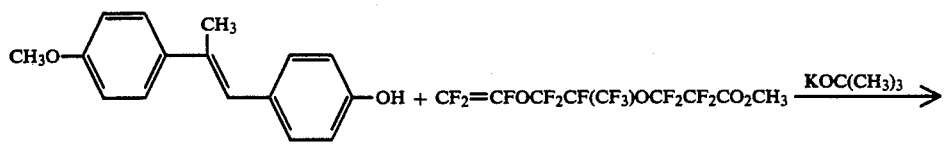

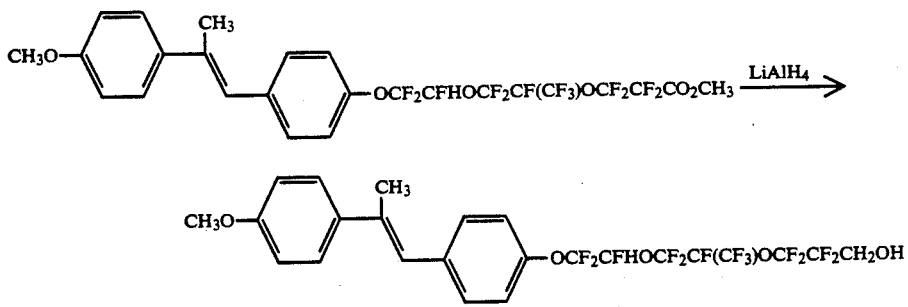

To a solution of 20.98 g (0.087 mol) of 4-methoxy-4'-hydroxy-α-methylstilbene in 250 mL of DMF at 15° C. was added 0.43 g (0.0038 mol) of potassium t-butoxide, followed over the course of 1 hour by 55.3 g (0.131 mol) of EVE in 50 mL of THF. The resulting solution was stirred for 1 hour at 18°-20° C. and poured into ice water containing 5 mL of concentrated hydrochloric acid. The aqueous mixture was extracted with ether. The ether extracts were dried over anhydrous magnesium sulfate and concentrated on a rotary evaporator. The residue was slurried in hexane and the solid collected to give 18.22 g of unreacted 4-methoxy-4'-hydroxy-α-methylstilbene. The hexane solution was concentrated on a rotary evaporator to give 11.6 g of oil which was identified as containing the title ester by its NMR spectrum. The product in 25 mL of ether was added dropwise to 3.03 g of lithium aluminum hydride in 150 mL of ether at 0° C. This mixture was stirred for 5 hours at room temperature. It was hydrolyzed at 0° C. by addition of 3 mL of water, 3 mL of 15% sodium hydroxide solution and 9 mL of water and filtered. The solid was rinsed with ether. The combined ether solutions were dried over anhydrous magnesium sulfate and evaporated to an opaque oil. This material was combined with the product formed by similar reaction of 18.2 g of 4-methoxy-4'-hydroxy-α-methylstilbene, 1.35 g of potassium t-butoxide and 57.4 g of EVE, followed by reduction with 13.76 g of lithium aluminum hydride. The combined products were dissolved in 1% ethyl acetate in hexane and passed through a column of silica gel packed in hexane. The column was eluted with 1 L each of 5, 10, 15, 20 and 25% of ethyl acetate in hexane. From the 15 and 20% fractions was isolated 49.22 g of material which was Kugelrohr distilled at 190°-199° C. and 0.3 mm pressure to give 44.4 g of white solid, mp 60°-61° C., which was identified as the desired alcohol. Proton NMR (δ, CD$_2$Cl$_2$) 2.17 (dt, 1H); 2.24 (d, 3H); 3.81 (s, 3H); 4.04 (td, 2H); 6.15 (dt, 1H); 6.76 (s, 1H); 6.91 (d, 2H); 7.19 (d, 2H); 7.38 (d, 2H); 7.48 (d, 2H). Fluorine NMR (δ, CD$_2$Cl$_2$) −80.11 (3F, CF$_3$); −82.8 to −87.4 (6F, CF$_2$'s); −126.7 (2F, CF2); −144.81 (1F; CFH); −145.47 (1F, CF). Anal. Calcd. for C$_{24}$H$_{19}$F$_{13}$O$_5$: C, 45.44; H, 3.02; F, 38.93. Found: C, 45.38; H, 2.93; F, 39.66.

EXAMPLE 6

Synthesis of the Addition Product of EVE to Phenol and Reduction to the Corresponding Alcohol

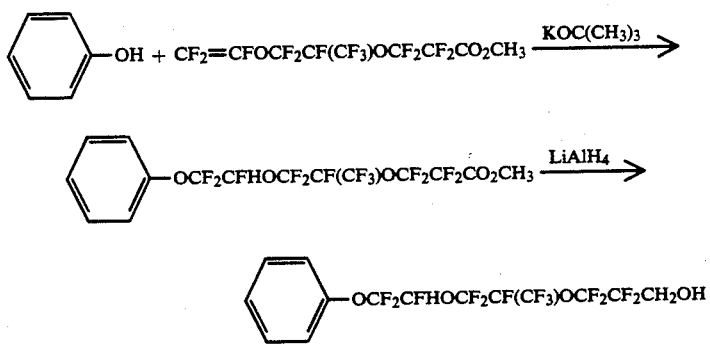

To a solution of 4.71 g (0.05 mol) phenol in 100 mL DMF was added 1.12 g (0.01 mol) potassium t-butoxide. EVE (24.1 g, 0.057 mol) was added dropwise over 0.5 hours at 22°-24° C. The resulting solution was stirred for 4.5 hours at room temperature, then poured into 500 mL of ice water containing 4 mL of concentrated hydrochloric acid. A lower layer was separated and the upper aqueous solution was extracted with 2×30 mL of methylene chloride. The combined organic layers were washed with 50 mL of ice water, dried over anhydrous magnesium sulfate and concentrated on a rotary evaporator at 12 mm to give 28.06 g of residue. Kugelrohr distillation at 0.5 mm and 113°-124° C. gave, after a small forerun, 18.5 g (72%) of the ester product. Proton NMR (δ, CDCl$_3$) 3.93 (s, 3H); 6.06 (doubled triplet, 1H); 7.20 (d, 2H); 7.28 (m, 1H); 7.38 (m, 2H). Fluorine NMR (δ, CDCl$_3$) −80.5 (3F); −82.6 to −87.6 (6F); −121.7 (2F); −144.98 (1F); −145.57 (1F). The ester product dissolved in ether was added over 0.5 hours to a suspension of 3.66 g (0.0964 mol) of lithium aluminum hydride in 150 mL of ether at 0° C. The resulting mixture was stirred at room temperature for 20 hours. It was cooled to 0° C. and quenched by the dropwise addition of 3.7 mL of water, 3.7 mL of 15% aqueous sodium hydroxide solution and 12 mL of water. The mixture was filtered and concentrated on a rotary evaporator to a clear oil. Chromatography on a 230–400 mesh silica column with 2:3 hexane:methylene chloride give 16.3 g (93 %) of the product alcohol as a colorless liquid. Proton NMR (δ, CDCl$_3$) 2.28 (s, 1H); 4.0 (t, 2H); 6.06 (dt, 1H); 7.15–7.40 (m, 5H). Fluorine NMR (δ, CDCl$_3$) −80.47 (3F, CF$_3$); −83.2 to −87.6 (6F, CF$_2$'s); −126.7 (2F, CF$_2$); −145.1 (1F; CFH); −145.8 (1F, CF).

EXPERIMENT 1

Synthesis and Polymerization of a Methacrylate Derivative of an Aryloxyfluoroether Alcohol

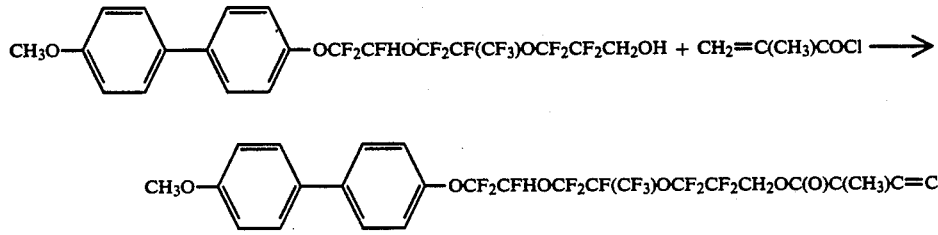

A solution of 1.15 g (0.011 mol) of methacryloyl chloride in 10 mL of methylene chloride and a solution of 1.11 g (0.11 mol) of triethylamine in methylene chloride were added simultaneously over 0.5 hr to a stirred solution of 5.94 g (0.010 mol) of the aryloxyfluoroether alcohol of Example 3 and 0.011 g of hydroquinone in 25 mL of methylene chloride at 0° C. The resulting mixture was stirred for 17 hr at room temperature. The mixture was cooled to 0° C. and 80 mL of water were added. The methylene chloride solution was separated, washed with water and aqueous sodium bicarbonate solution, dried over anhydrous sodium sulfate and concentrated on a rotary evaporator to 5.73 g of oil. A Kugelrohr distillation at 170°–180° C. and 0.1 mm pressure gave 4.96 g of the methacrylate. Proton NMR (δ,CD$_2$Cl$_2$) 1.95 (s, 3H); 3.85 (s, 3H); 4.6 (s, 2H); 5.68 (s, 1H); 6.18 (s, 1H); 6.18 (dt 1H); 6.9–7.6 (2q, 8H). Fluorine NMR (δ, CD$_2$Cl$_2$) −80.6 (3F); −83.5 to −88.0 (6F); −123.5 (2F); −145.4 (1F); −146.0 (1F). Anal: Calcd. for C25H19F13O6: C, 45.19; H, 3.19; F, 37.17. Found: C, 45.44; H, 3.02; F, 36.71.

A solution of 2.33 g of the above methacrylate was dissolved in 10 mL of benzene. The solution was deoxygenated by evacuating and filling with nitrogen twice. An argon purged solution of 23.6 mg of Vazo ®52 in 20 mL of benzene was added. The resulting solution was heated at 40° C. for 66 hr, then poured in methanol to give 1.02 g of polymer with number average molecular weight=34400 and weight average molecular weight=58400 by gel permeation chromatography, inherent viscosity in toluene =0.066 dL/g. Anal: Found: C, 45.3; H, 2.99; F, 36.48, 36.17.

Although preferred embodiments of the invention have been described hereinabove, it is to be understood that there is no attempt to limit the invention to the precise constructions herein disclosed, and that modifications to the invention may be made without departing from the specification and scope thereof.

What is claimed is:

1. A process for the production of aryloxyfluoroether esters, comprising, contacting a base, a perfluorovinylether ester of the formula CF$_2$=CFOR$^1$CO$_2$R$^2$ and a hydroxyaromatic compound of the formula Ar$_p$, wherein:

Ar is an organic radical containing one or more aromatic rings, which remains unchanged during the process;

Z is oxygen;

each R$^1$ is perfluoroalkyl or ether, thioether, chloro, hydrogen, alkyl, or phenyl substituted perfluoroalkyl; and p is 1, 2, 3, 4, or 5; and provided, that each Z is bonded to said aromatic rings.

2. The process as recited in claim 1 carried out in a solvent.

3. The process as recited in claim 2 wherein said solvent is selected from the group consisting of N,N-dimethylformamide, tetrahydrofuran, dimethyacetamide and dimethylsulfoxide and mixtures thereof.

4. The process as recited in claim 1 wherein the temperature is from about −20° C. to about 50° C.

5. The process as recited in claim 4 wherein the temperature is from about +20° C. to about 30° C.

6. The process as recited in claim 1 wherein Ar from the group consisting of phenyl, phenylene, biphenyl, 4,4'-biphenylene, naphthyl and 2-phenylethenylphenyl.

7. The process as recited in claim 1 wherein R$^1$ is —[CF$_2$CF(CF$_3$)O]$_n$(CF$_2$)$_m$—, wherein n is an integer from 0 through 5 and m is an integer from 1 through 10.

8. The process as recited in claim 7 wherein Ar is selected from the group consisting of phenyl, phenylene, biphenyl, 4,4'-biphenylene, naphthyl and 2-phenylethenylphenyl.

9. The process as recited in claim 1 wherein R$^2$ is selected from the group consisting of normal alkyl with up to 6 carbon atoms.

10. The process as recited in claim 1 wherein p is 1 or 2.

11. The process as recited in claim 7 wherein p is 1 or 2.

12. The process as recited in claim 6 wherein p is 1 or 2.

13. The process as recited in claim 8 wherein p is 1 or 2.

14. The process as recited in claim 10 carried out in a solvent at a temperature of about −20° C. to about 50° C.

15. The process as recited in claim 11 carried out in a solvent at a temperature of about −20° C. to about 50° C.

16. The process as recited in claim 12 carried out is solvent at a temperature of about −20° C. to about 50° C.

17. The process as recited in claim 13 carried out in a solvent at a temperature of about −20° C. to about 50° C.

18. The process as recited in claim 2 wherein the temperature is about −20° C. to about 50° C.

19. The process as recited in claim 1 carried out under an inert atmosphere.

20. The process as recited in claim 19 wherein the inert atmosphere is selected from the group consisting of nitrogen and argon.

21. The process as recited in claim 1 wherein the base is selected from the group consisting of alkali metal hydrides and alkali metal alkoxides.

22. The process as recited in claim 1 wherein the base is present in an amount up to approximately equimolar with the —ZH groups present.

23. The process as recited in claim 22 wherein the base is present in a molar amount equal to about 1% to about 20% of the —ZH groups present.

24. The process as recited in claim 2 wherein the base is present in a molar amount equal to about 1% to about 20% of the —ZH groups present.

25. The process as recited in claim 4 wherein the base is present in a molar amount equal to about 1% to about 20% of the —ZH groups present.

26. The process as recited in claim 18 wherein the base is present in a molar amount equal to about 1% to about 20% of the —ZH groups present.

27. The process as recited in claim 1 wherein the pKa of said hydroxyaromatic compound is about 5 to about 12.

28. The process as recited in claim 22 wherein the pKa of said hydroxyaromatic compound is about 5 to about 12.

29. The process as recited in claim 23 wherein the said hydroxyaromatic compound is about 5 to about 12.

30. The process as recited in claim 2 wherein the pKa of said hydroxyaromatic compound is about 5 to about 12.

31. The process as recited in claim 24 wherein the pKa of said hydroxyaromatic compound is about 5 to about 12.

32. The process as recited in claim 4 wherein the pKa of said hydroxyaromatic compound is about 5 to about 12.

33. The process as recited in claim 25 wherein the pKa of said hydroxyaromatic compound is about 5 to about 12.

34. The process as recited in claim 18 wherein the pKa of said hydroxyaromatic compound is about 5 to about 12.

35. The process as recited in claim 26 wherein the pKa of said hydroxyaromatic compound is about 5 to about 12.

* * * * *